(12) United States Patent
Yamanobe et al.

(10) Patent No.: US 8,562,916 B2
(45) Date of Patent: Oct. 22, 2013

(54) MEDICAL WASTES DISPOSAL APPARATUS AND MEDICAL WASTES DISPOSAL METHOD

(76) Inventors: Yoichiro Yamanobe, Iwaki (JP); Kenki Hosoi, Fukushima (JP)

( * ) Notice: Subject to any disclaimer, the term of this patent is extended or adjusted under 35 U.S.C. 154(b) by 0 days.

(21) Appl. No.: 13/354,462

(22) Filed: Jan. 20, 2012

(65) Prior Publication Data
US 2013/0189155 A1 Jul. 25, 2013

(51) Int. Cl.
*A01H 5/02* (2006.01)
*A61L 2/04* (2006.01)
*B02B 1/08* (2006.01)

(52) U.S. Cl.
USPC ............................ 422/309; 422/307; 241/606

(58) Field of Classification Search
USPC .................................. 241/606; 422/309, 307
See application file for complete search history.

(56) References Cited

U.S. PATENT DOCUMENTS 5,972,291 A * 10/1999 Healy et al. ..................... 422/22

FOREIGN PATENT DOCUMENTS

| JP | 04-327848 | 11/1992 |
|----|-----------|---------|
| JP | 6-42819 | 6/1994 |
| JP | 07-88140 | 4/1995 |
| JP | 2001-252345 | 9/2001 |
| JP | 2003-116938 | 4/2003 |
| JP | 2003-190229 | 7/2003 |
| JP | 2004-298585 | 10/2004 |
| JP | 3126377 | 10/2006 |
| JP | 2008-000558 | 1/2008 |
| JP | 2008-000734 | 1/2008 |
| JP | 2008-000735 | 1/2008 |
| JP | 2011-235278 | 11/2011 |

OTHER PUBLICATIONS

International Search Report and Written Opinion dated Apr. 24, 2012 in corresponding PCT/JP2012/051506 (ten pages).

* cited by examiner

*Primary Examiner* — Kevin Joyner
(74) *Attorney, Agent, or Firm* — Harness, Dickey & Pierce, P.L.C.

(57) ABSTRACT

When a polyethylene bag with medical wastes received therein is supplied to a cylindrical-shaped housing and a compression device is used to lower a piston to compress the medical wastes, the piston is repeatedly caused to go up and down to accomplish stepwise compression whereby the polyethylene bag with medical wastes received therein is prevented from entering into a clearance between an inner wall of the cylindrical-shaped housing and the piston and from bursting due to rapid compression, and when cake obtained by melt sterilization and volume reduction with heating compression is discharged, a gate is fully opened to lower a lower surface of a heating device of the piston to a point distant several millimeters from an upper surface of a heating device of the gate to enable forcedly scraping off the cake adhering to the heating device tightly joined to the piston upon closing of the gate.

10 Claims, 7 Drawing Sheets

MEDICAL WASTES DISPOSAL APPARATUS AND MEDICAL WASTES DISPOSAL METHOD

TECHNICAL FIELD

The present invention relates to a medical wastes disposal apparatus, in which infectious medical wastes generated in medical institutions such as hospitals or the like are subjected to sterilization and volume reduction and made harmless, and a medical wastes disposal method.

BACKGROUND ART

Several methods, such as incineration disposal, crushing sterilization by medicament disposal, sterilization by autoclave heat disposal, microwave ashing disposal, high-temperature plasma disposal, etc., have been proposed as a disposal method of infectious medical wastes, but these proposals involve the following problems and cannot be said to be adequate.

While the incineration disposal being a typical disposal method of infectious medical wastes has a feature that when medical wastes are incinerated, only ash remains and the disposal is very high in rate of volume reduction, a secondary combustion furnace, a waste gas quench apparatus, an electrical dust precipitator, a bag filter, a device for analysis and monitoring of exhaust gases, etc. are essential in order to prevent generation of dioxin, and in the case where these devices are not provided, a serious problem from the view point of environmental protection and energy activation remains in a sense that there is a fear of great atmospheric pollution caused by a large amount of hydrogen chloride gas generated from vinyl chloride resin contained in medical wastes and medical wastes being valuable in energy recycling are incinerated wastefully.

Also, the crushing sterilization by medicament disposal involves a serious problem from the view point of reliability in sterilization and environmental protection since there is a fear that pathogenic bacteria contained in medical wastes scatter into the atmosphere when medical wastes are crushed, even when it is tried to crush medical wastes to subject them to sterilization by medicament, the possibility of sure sterilization of pathogenic bacteria existent in fluid infusion tubes or the like is not guaranteed, and there is a fear that medical wastes being minutely crushed in a reclaimed disposal site are scattered by wind to forest land and farmland.

Further, the sterilization by autoclave heat disposal is thought in the light of Pascal's formula to enable materializing uniform pressure and uniform temperature in all locations in an autoclave to enable sure sterilization of medical wastes but involves a serious problem from the view point of reliability in sterilization and working environment since it is heard from the scene that sterilization cannot be completely accomplished and grotesque medical wastes are handled after the sterilization disposal while being in the original form.

Also, the microwave ashing disposal makes use of the principle of home electronic oven but cannot be said to be an actual disposal in terms of increased installation cost since the disposal is not only low in processing capacity but also a waste gas processing device is essential like the incineration disposal described above, to say nothing of ensuring the corrosion resistance for the apparatus, since a large amount of hydrogen chloride gas is generated when vinyl chloride wastes contained in medical wastes are subjected to ashing disposal.

Further, the high-temperature plasma disposal cannot be said to be an actual disposal in terms of increased installation cost since not only the operation of an apparatus in temperature as high as 3000° C. needs a high operation technology but also a waste gas processing device is essential like the incineration disposal described above, to say nothing of ensuring the corrosion resistance for the apparatus, since a large amount of hydrogen chloride gas is generated when vinyl chloride wastes contained in medical wastes are subjected to plasma disposal.

Further, in order to solve a problem involved in a heating and melting system or crushing sterilization by medicament system disposal method for infectious medical wastes, JP-A-7-88140 discloses a disposal apparatus for making medical wastes harmless, the apparatus comprising a substrate, from which medical wastes are forwarded in the form of compact cake, a housing provided on the substrate and having a discharge passage of cake, an upright cylinder arranged on the housing and provided with a charging port for medical wastes and a swingable push lid, a first piston unit provided on the cylinder and having a piston, which compresses medical wastes into cake, a second piston unit provided on the substrate and having a moving plate for opening and closing of a drop port of the cylinder, and an evaporation unit arranged on the substrate below the housing.

Also, JP-U-6-42819 discloses, as a bucket conveyor obtained by improving a conveyor, a bucket conveyor, in which a drive shaft provided at both ends thereof with driving wheels is borne at one end of a base frame, a driven shaft provided at both ends thereof with driven wheels is borne at the other end of the base frame, one end of the drive shaft is connected to a motor through a reduction device, L-shaped partition plates, respectively, are mounted in opposite and back to back manner to an upper surface of an endless belt, which turns in a manner of enabling stepping rotation, between the driving wheels and the driven wheels, side plates, respectively, are mounted on both side upper portions of the base frame in a manner to substantially contact both ends of the partition plates, and notches, which are shaped to agree with the cross sectional shape of a basket portion defined by a pair of the partition plates, are provided at one ends of the both side plates.

Further, in order to solve a problem involved in a disposal method of heating and melting system for infectious medical wastes, JP-A-2001-252345 discloses a disposal apparatus for making medical wastes harmless, the apparatus comprising a bucket conveyor section (3) for transporting a plurality of buckets (2), which store bag bodies (P) receiving therein medical wastes (M), while steppingly rotating them in a predetermined direction, a sterilization by heat section (4, 4a), by which medical wastes stored in a bucket are subjected to sterilization by heat, a compression disposal section (5), by which medical wastes having been subjected to sterilization by heat are compressed in a position after the sterilization by heat section to make a cake-like substance (C), and a discharge section (7) for discharge of the cake-like substance from the compression disposal section, the apparatus having a feature that a bag body with medical wastes received therein is received in the bucket (2) positioned inside side plates (9) arranged in a traveling direction of the bucket conveyor section (3), a plurality of heat feed pipes (23) having a plurality of small holes on peripheral surfaces of lower portions thereof and exhaust pipes (25) are provided in a track of the bucket conveyor section, a hot air blasting device (24) is provided on the heat feed pipes, and the heat feed pipes and the exhaust pipes are pushed down by a hydraulic cylinder to blow a hot blast from the heat feed pipes, which are pierced into the bag body, to accomplish sterilization by heat.

Also, in order to solve that matter, in which when heating-compressing means is used to subject medical wastes generated in medical institutions to sterilization-volume reduction, the wastes are caused by pressure to adhere to a heating element, which comprises heating means, to make discharge difficult, JP-U-3126377 discloses a disposed product discharging mechanism in a medical wastes disposal apparatus comprising a disposal cylinder (4), a piston (13) provided with means, which goes up and down in the disposal cylinder (4), and having an electric heater (14), and a gate (16) provided with means, which opens and closes a lower end opening of the disposal cylinder (4), and having an electric heater (17), the mechanism having a feature that after medical wastes are subjected to sterilization volume reduction by heating compression, the gate (16) is fully opened to lower a lower end surface of the electric heater (14) of the piston (13) to an upper end surface of the electric heater (17) of the gate (16) to fully close the gate (16) and a disposed product adhering to the electric heater (14) of the piston (13) is mechanically scraped off.

SUMMARY OF THE INVENTION

Technical Problem

It is an object of the invention to solve various problems involved in the prior medical wastes disposal apparatuses and medical wastes disposal methods described above and further improve the prior medical wastes disposal apparatuses and medical wastes disposal methods and to provide a high medical wastes disposal method and a high medical wastes disposal apparatus capable of meeting all work safety ensuring, pollution control of atmosphere and water quality, nature environmental maintenance, energy recycling, etc., to say nothing of sure disposal of sterilization and volume reduction.

In order to solve the above problems, the invention according to claim 1 has a feature in a medical wastes disposal apparatus comprising a gate including heating means and opening and closing means on a housing lower portion of a vertical-type cylindrical-shaped housing opened at both upper and lower ends thereof, a piston including heating means and compression means based on ascent and descent on an upper portion of the housing, and a hatch including opening and closing means for opening and closing of a side opening provided on a side of the housing, and wherein when a polyethylene bag with medical wastes received therein is supplied to the cylindrical-shaped housing and the compression means lowers the piston to compress the medical wastes, the piston is repeatedly caused to go up and down for stepwise compression whereby the polyethylene bag with medical wastes received therein is prevented from entering into a clearance between an inner wall of the cylindrical-shaped housing and the piston and from bursting due to rapid compression, and when cake obtained by melt sterilization and volume reduction with heating compression is discharged, the gate is fully opened to lower a lower surface of the heating means of the piston to a point distant several millimeters from an upper surface of the heating means of the gate and the gate is closed to enable forcedly scraping off cake adhering to the heating means tightly joined to the piston.

The invention according to claim 2 adds to the medical wastes disposal apparatus according to claim 1 a feature in further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower.

The invention according to claim 3 adds to the medical wastes disposal apparatus according to claim 1 a feature in further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and in that whenever a polyethylene bag, a polypale, or cans, etc., in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, and a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and in that the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate.

The invention according to claim 4 adds to the medical wastes disposal apparatus according to claim 1 a feature in further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and in that whenever a polyethylene bag, a polypale, or cans, etc., in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and in that the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein it is possible to subject medical wastes to disposal of sterilization by heat only with hot blast by means of the medical wastes preheating device, to discharge the medical wastes from the bucket conveyor not via the medical wastes disposal apparatus, and to manually classify contents of the medical wastes into vinyl chloride series and non-vinyl chloride series.

The invention according to claim 5 adds to the medical wastes disposal apparatus according to claim 1 a feature in that a nitrogen gas supply pipe provided with an electrically shut-off electromagnetic valve is further connected by way of piping to a piercing nozzle for hot air blasting, which nozzle is tightly joined to a moving plate provided with ascent and descent means, which is capable of going up and down in the vertical direction, a thermometer for detection of abnormal temperature rise of exhaust gases is further provided on a piercing nozzle for exhausting, and in the case where hot blast is blown into a polyethylene bag and a polypalre to thereby originate a fire in an oxygen scavenger mixed into medical wastes to cause a fire, the thermometer detects abnormal temperature rise of exhaust gases and the electromagnetic valve on the nitrogen gas supply pipe is electrically interlockingly opened to permit nitrogen gases to be blown into the polyethylene bag and the polypale whereby it is possible to automatically extinguish a fire caused in the polyethylene bag and the polypale.

The invention according to claim 6 adds to the medical wastes disposal apparatus according to claim 1 a feature in further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and in that whenever a polyethylene bag, a polypale, or cans, etc., in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and in that the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, and holes, for photoelectric switches, provided on the same axis on both sides of the side guide plates of the bucket conveyor, and a pair of photoelectric switches arranged in positions, in which light can transmit through the holes, in the holes of the side guide plates and in that the photoelectric switches detect the presence of a polyethylene bag, a polypale, or cans, etc., in which medical wastes are received, in a bucket of the bucket conveyor to enable automatically and sequentially stopping the medical wastes preheating device, the bucket conveyor, and the medical wastes disposal apparatus at the completion of disposals of a predetermined number of cycles.

The invention according to claim 7 adds to the medical wastes disposal apparatus according to claim 1 a feature in further comprising a side hole provided on the lower portion of the vertical-type cylindrical-shaped housing and a fork mechanism provided with drawing and entering means, which is capable of drawing out of and entering into the side hole and in that when a polypale or cans, etc., in which medical wastes are received, are fed from the side opening on the side of the vertical-type cylindrical-shaped housing, a fork of the fork mechanism is caused to advance into an interior of the housing to receive the polypale or cans on the fork, and after the hatch for the side opening is closed, the fork is caused to retreat to enable loading the polypale or cans on the gate, which is disposed on the housing lower portion, without tipping.

The invention according to claim 8 adds to the medical wastes disposal apparatus according to claim 1 a feature in further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and in that whenever a polyethylene bag, a polypale, or cans, etc., in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and in that the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein a friction type blower is further provided on the hot blast generating device of the medical wastes preheating device to enable preheating an air by means of frictional heat generated in the friction type blower to reduce electric energy for air heating in the hot blast generating device.

The invention according to claim 9 adds to the medical wastes disposal apparatus according to claim 1 a feature in further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and in that whenever a polyethylene bag, a polypale, or cans, etc., in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and in that the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein in a process, in which the piercing nozzles for hot air blasting and for exhausting, tightly joined to the moving plate provided with ascent and descent means, which is capable of going up and down in the vertical direction of the medical wastes preheating device, are caused to pierce a polyethylene bag or a polypale to bring about preheating, the moving plate goes up and down at all times to enable evenly heating medical wastes in the polyethylene bag or the polypale.

The invention according to claim 10 adds to the medical wastes disposal apparatus according to claim 1 a feature in further comprising a drain-board arranged below the gate on the lower portion of the vertical-type cylindrical-shaped housing to receive cake obtained by melt sterilization and volume reduction of medical wastes with heating compression and a push plate tightly joined to the gate to enable maintaining a predetermined spacing between it and the drain-board and in that cake dropping upon opening of the gate can be automatically discharged outside by the push plate tightly joined to the gate when the gate is closed.

The invention according to claim 11 adds to the medical wastes disposal apparatus according to claim 1 a feature in further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and in that whenever a polyethylene bag, a polypale, or cans, etc., in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and in that the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, and a bar code or a quick response code is further stuck to medical wastes, which are received in a polyethylene bag, a polypale, cans, etc., every department of diagnosis and treatment, from which the medical wastes are discharged, when the medical wastes are loaded in the bucket of the bucket conveyor, the bar code or quick response code is read, and after the medical wastes are subjected to disposal of melt sterilization and volume reduction with heating compression, the information of emission source, disposal conditions of the medical wastes preheating device and the medical wastes disposal apparatus, etc. are automatically written on an electronic tag and the electronic tag is automatically stuck to cake, which is obtained by disposal, by means of an IC tag sticking device to enable certifying that the medical wastes have been properly subjected to disposal.

The invention according to claim 12 adds to the medical wastes disposal apparatus according to claim 1 a feature in further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and in that whenever a polyethylene bag, a polypale, or cans, etc., in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and in that the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein the bucket conveyor, the medical wastes preheating device, and the medical wastes disposal apparatus are electrically interlocked to enable exercising integrated control by means of a programmable sequencer and a touch panel display electrically interlocked with the programmable sequencer.

The invention according to claim 13 has a feature in a medical wastes disposal method comprising the step of supplying a polyethylene bag with medical wastes received therein to a vertical-type cylindrical-shaped housing opened at both upper and lower ends thereof, the step of repeatedly causing a piston to go up and down for stepwise compression to thereby prevent the polyethylene bag with medical wastes received therein from entering into a clearance between an inner wall of the cylindrical-shaped housing and the piston and from bursting due to rapid compression, when compression means of the piston including heating means and the compression means based on ascent and descent, on an upper portion of the housing lowers the piston to compress the medical wastes, the step of fully opening a gate, which includes heating means and opening and closing means on a housing lower portion of the housing, when cake obtained by melt sterilization and volume reduction with heating compression is discharged, and the step of lowering a lower surface of the heating means of the piston to a point distant several millimeters from an upper surface of the heating means of the gate and closing the gate to enable forcedly scraping off cake adhering to the heating means tightly joined to the piston.

The invention according to claim 14 has a feature in a medical wastes disposal method comprising the step of supplying a polyethylene bag with medical wastes received therein to a vertical-type cylindrical-shaped housing opened at both upper and lower ends thereof, the step of repeatedly causing a piston to go up and down for stepwise compression to thereby prevent the polyethylene bag with medical wastes received therein from entering into a clearance between an inner wall of the cylindrical-shaped housing and the piston and from bursting due to rapid compression, when compression means of the piston including heating means and the compression means based on ascent and descent, on an upper portion of the housing lowers the piston to compress the medical wastes, the step of fully opening a gate, which includes heating means and opening and closing means on a housing lower portion of the housing, when cake obtained by melt sterilization and volume reduction with heating compression is discharged, and the step of lowering a lower surface of the heating means of the piston to a point distant several millimeters from an upper surface of the heating means of the gate and closing the gate to enable forcedly scraping off cake adhering to the heating means tightly joined to the piston, the step of sucking gases generated in the course of heating and compressing medical wastes with a blower connected by way of piping to a nozzle provided on the housing upper portion of the vertical-type cylindrical-shaped housing to be capable of air ventilation in the housing and a nozzle provided outside and above gate opening and closing means for opening and closing of the housing lower portion to be capable of air ventilation above the gate, the step of deodorizing gases by means of deodorizing means at a discharge port of the blower, and the step of filtering pathogenic bacteria by means of filtering means at the discharge port of the blower.

The invention according to claim 15 has a feature in a medical wastes disposal method comprising the step of supplying a polyethylene bag with medical wastes received therein to a vertical-type cylindrical-shaped housing opened at both upper and lower ends thereof, the step of repeatedly causing a piston to go up and down for stepwise compression to thereby prevent the polyethylene bag with medical wastes received therein from entering into a clearance between an inner wall of the cylindrical-shaped housing and the piston and from bursting due to rapid compression, when compression means of the piston including heating means and the compression means based on ascent and descent, on an upper portion of the housing lowers the piston to compress the medical wastes, the step of fully opening a gate, which includes heating means and opening and closing means on a housing lower portion of the housing, when cake obtained by melt sterilization and volume reduction with heating compression is discharged, and the step of lowering a lower surface of the heating means of the piston to a point distant several millimeters from an upper surface of the heating means of the gate and closing the gate to enable forcedly scraping off cake adhering to the heating means tightly joined to the piston, the step of sucking gases generated in the course of heating and compressing medical wastes with a blower connected by way of piping to a nozzle provided on the housing upper portion of the vertical-type cylindrical-shaped housing to be capable of air ventilation in the housing and a nozzle provided outside and above gate opening and closing means for opening and closing of the housing lower portion to be capable of air ventilation above the gate, the step of deodorizing gases by means of deodorizing means at a discharge port of the blower, and the step of filtering pathogenic bacteria by means of filtering means at the discharge port of the blower, the step of loading a polyethylene bag, a polypale, or cans, etc., in which medical wastes are received, in a bucket of a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the step of causing the bucket conveyor to advance one bucket by one bucket and stop whenever a disposal cycle of medical wastes is completed in the medical wastes disposal apparatus, the step of automatically feeding the medical wastes loaded in the bucket to the medical wastes disposal apparatus by means of a pusher mechanism of an automatic feeding device, which comprises the pusher mechanism for transfer to the housing side opening of the medical wastes disposal apparatus from a side guide plate opening at a terminal end in the traveling direction of the bucket conveyor, and the step of causing the bucket conveyor, when abnormality is caused in the bucket conveyor, to continuously advance or retreat to enable taking out the medical wastes loaded in the bucket of the bucket conveyor, the step of piercing piercing nozzles, for hot air blasting and for exhausting, of a medical wastes preheating device, which is formed by tightly joining the piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, into a polyethylene bag and a polypale, in which medical wastes are received and which are loaded in the bucket of the bucket conveyor, to preheat the medical wastes by hot air blasting of the hot blast generating device to achieve shortening in cycle time, and the step of using a cover with an exhaust nozzle to cover the periphery of a moving plate provided with ascent and descent means, which is capable of going up and down in the vertical direction, and connecting the exhaust nozzle of the cover by way of piping to a suction port of a blower provided at an exhaust port thereof with deodorizing means for deodorization of gases and filtering means for filtration of pathogenic bacteria, thereby enabling deodorizing and filtering exhaust gases generated from the piercing nozzle, for exhaust, tightly joined to the moving plate.

The invention according to claim 16 adds to the medical wastes disposal method according to claim 15 a feature in further comprising the step of subjecting medical wastes to disposal of sterilization by heat only with hot blast by means of the medical wastes preheating device, and the step of discharging the medical wastes from the bucket conveyor not via the medical wastes disposal apparatus, so that it is possible to manually classify contents of the medical wastes into vinyl chloride series and non-vinyl chloride series.

The invention according to claim 17 adds to the medical wastes disposal method according to claim 13 a feature in further comprising the step of detecting abnormal temperature rise of exhaust gases by means of a thermometer provided on a piercing nozzle, for exhausting, for detection of abnormal temperature rise of exhaust gases in the case where hot blast is blown into a polyethylene bag and a polypale to thereby originate a fire in an oxygen scavenger mixed into medical wastes to cause a fire, and the step of permitting an electrically shut-off electromagnetic valve on the nitrogen gas supply pipe provided with the electromagnetic valve to be opened electrically interlocking with a piercing nozzle for hot air blasting, which nozzle is tightly joined to a moving plate provided with ascent and descent means, which is capable of going up and down in the vertical direction, to permit nitrogen gases to be blown into the polyethylene bag and the polypale whereby it is possible to automatically extinguish a fire caused in the polyethylene bag and the polypale.

The invention according to claim 18 adds to the medical wastes disposal method according to claim 14 a feature in further comprising the step of detecting abnormal temperature rise of exhaust gases by means of a thermometer provided on a piercing nozzle, for exhausting, for detection of abnormal temperature rise of exhaust gases in the case where hot blast is blown into a polyethylene bag and a polypale to thereby originate a fire in an oxygen scavenger mixed into medical wastes to cause a fire, and the step of permitting an electrically shut-off electromagnetic valve on the nitrogen gas supply pipe provided with the electromagnetic valve to be opened electrically interlocking with a piercing nozzle for hot air blasting, which nozzle is tightly joined to a moving plate provided with ascent and descent means, which is capable of going up and down in the vertical direction, to permit nitrogen gases to be blown into the polyethylene bag and the polypale whereby it is possible to automatically extinguish a fire caused in the polyethylene bag and the polypale.

The invention according to claim 19 adds to the medical wastes disposal method according to claim 15 a feature in further comprising the step of detecting abnormal temperature rise of exhaust gases by means of a thermometer provided on a piercing nozzle, for exhausting, for detection of abnormal temperature rise of exhaust gases in the case where hot blast is blown into a polyethylene bag and a polypale to thereby originate a fire in an oxygen scavenger mixed into medical wastes to cause a fire, and the step of permitting an electrically shut-off electromagnetic valve on the nitrogen gas supply pipe provided with the electromagnetic valve to be opened electrically interlocking with a piercing nozzle for hot air blasting, which nozzle is tightly joined to a moving plate provided with ascent and descent means, which is capable of going up and down in the vertical direction, to permit nitrogen gases to be blown into the polyethylene bag and the polypale whereby it is possible to automatically extinguish a fire caused in the polyethylene bag and the polypale.

The invention according to claim 20 adds to the medical wastes disposal method according to claim 15 a feature in further comprising the step of detecting the presence of a polyethylene bag, a polypale, or cans, etc., in which medical wastes are received, in a bucket of the bucket conveyor by means of a pair of photoelectric switches arranged in positions, in which light can transmit through holes, for photoelectric switches, provided on the same axis on both sides of the side guide plates of the bucket conveyor, and the step of enabling automatically and sequentially stopping the medical wastes preheating device, the bucket conveyor, and the medical wastes disposal apparatus at the completion of disposals of a predetermined number of cycles.

The invention according to claim 21 adds to the medical wastes disposal method according to claim 13 a feature in further comprising the step of causing a fork of a fork mechanism provided with drawing and entering means, which is capable of drawing out of and entering into a side hole provided on the lower portion of the vertical-type cylindrical-shaped housing, to advance into an interior of the housing to receive the polypale or cans on the fork, when a polypale or cans, etc., in which medical wastes are received, are fed from a side opening on the side of the vertical-type cylindrical-shaped housing, and the step of causing the fork to retreat after a hatch for the side opening is closed, whereby the polypale or cans can be loaded on the heating means of the gate, which is disposed on the housing lower portion, without tipping.

The invention according to claim 22 adds to the medical wastes disposal method according to claim 14 a feature in further comprising the step of causing a fork of a fork mechanism provided with drawing and entering means, which is capable of drawing out of and entering into a side hole provided on the lower portion of the vertical-type cylindrical-shaped housing, to advance into an interior of the housing to receive the polypale or cans on the fork, when a polypale or cans, etc., in which medical wastes are received, are fed from a side opening on the side of the vertical-type cylindrical-shaped housing, and the step of causing the fork to retreat after a hatch for the side opening is closed, whereby the polypale or cans can be loaded on the heating means of the gate, which is disposed on the housing lower portion, without tipping.

The invention according to claim 23 adds to the medical wastes disposal method according to claim 15 a feature in further comprising the step of causing a fork of a fork mechanism provided with drawing and entering means, which is capable of drawing out of and entering into a side hole provided on the lower portion of the vertical-type cylindrical-shaped housing, to advance into an interior of the housing to receive the polypale or cans on the fork, when a polypale or cans, etc., in which medical wastes are received, are fed from a side opening on the side of the vertical-type cylindrical-shaped housing, and the step of causing the fork to retreat after a hatch for the side opening is closed, whereby the polypale or cans can be loaded on the heating means of the gate, which is disposed on the housing lower portion, without tipping.

The invention according to claim 24 adds to the medical wastes disposal method according to claim 15 a feature in further comprising the step of preheating an air by means of frictional heat generated in a friction type blower provided on the hot blast generating device of the medical wastes preheating device to enable reducing electric energy for air heating in the hot blast generating device.

The invention according to claim 25 adds to the medical wastes disposal method according to claim 15 a feature in further comprising the step of permitting the moving plate to go up and down at all times to enable evenly heating medical wastes in a polyethylene bag or a polypale in a process, in which the piercing nozzles for hot air blasting and for exhausting, tightly joined to the moving plate provided with ascent and descent means, which is capable of going up and down in the vertical direction of the medical wastes preheating device, are caused to pierce the polyethylene bag or the polypale to bring about preheating.

The invention according to claim 26 adds to the medical wastes disposal method according to claim 13 a feature in further comprising the step of enabling automatically discharging cake dropping upon opening of the gate outside by means of the push plate, which is tightly joined to the gate to enable maintaining a predetermined spacing between it and the drain-board arranged below the gate on the lower portion of the vertical-type cylindrical-shaped housing to receive cake obtained by melt sterilization and volume reduction of medical wastes with heating compression, when the gate is closed.

The invention according to claim 27 adds to the medical wastes disposal method according to claim 14 a feature in further comprising the step of enabling automatically discharging cake dropping upon opening of the gate outside by means of the push plate, which is tightly joined to the gate to enable maintaining a predetermined spacing between it and the drain-board arranged below the gate on the lower portion of the vertical-type cylindrical-shaped housing to receive cake obtained by melt sterilization and volume reduction of medical wastes with heating compression, when the gate is closed.

The invention according to claim 28 adds to the medical wastes disposal method according to claims 15 a feature in further comprising the step of enabling automatically discharging cake dropping upon opening of the gate outside by means of the push plate, which is tightly joined to the gate to enable maintaining a predetermined spacing between it and the drain-board arranged below the gate on the lower portion of the vertical-type cylindrical-shaped housing to receive cake obtained by melt sterilization and volume reduction of medical wastes with heating compression, when the gate is closed.

The invention according to claim 29 adds to the medical wastes disposal method according to claim 15 a feature in further comprising the step of reading a bar code or a quick response code stuck to medical wastes, which are received in a polyethylene bag, a polypale, cans, etc., every department of diagnosis and treatment, from which the medical wastes are discharged, when the medical wastes are loaded in the bucket of the bucket conveyor, and the step of automatically writing the information of emission source, disposal conditions of the medical wastes preheating device and the medical wastes disposal apparatus, etc. on an electronic tag after the medical wastes are subjected to disposal of melt sterilization and volume reduction with heating compression, and automatically sticking the electronic tag to cake, which is obtained by disposal, by means of an IC tag sticking device to enable certifying that the medical wastes have been properly subjected to disposal.

The invention according to claim 30 adds to the medical wastes disposal method according to claim 15 a feature in further comprising the step of electrically interlocking the bucket conveyor, the medical wastes preheating device, and the medical wastes disposal apparatus to enable exercising integrated control by means of a programmable sequencer and a touch panel display electrically interlocked with the programmable sequencer.

Effect of the Invention

The invention enables heating and compressing infectious medical wastes to surely subject them to disposal of melt sterilization and volume reduction. Also, since being free from a fear such as environment pollution or the like and simple in operation, the present apparatus can be installed in a hospital to subject infectious medical wastes to disposal in the hospital, the hospital can completely eliminate a risk of assuming a responsibility of an emission source in the case where the hospital entrusts disposal of infectious medical wastes to an unidentified wastes disposal trader and the trader abandons the wastes illegally, and can fulfill a social responsibility as a hospital. Further, there is produced an effect that cake obtained by disposal of infectious medical wastes can be put to energy recycling as a blast furnace reducing material in ironmaking factories and a fuel in cement factories and the apparatus can greatly contribute to social welfare as a most excellent medical wastes disposal apparatus from the viewpoint of resource energy.

The invention according to claims 1 and 13 produces an effect that since the piston is repeatedly caused to go up and down to thereby enable stepwise heating and compressing a polyethylene bag with medical wastes received therein, the polyethylene bag with medical wastes received therein is heated and compressed while gradually softening together with medical wastes, and compression can be accomplished while appropriately exhausting an air in the bag upon ascent of the piston even when the polyethylene bag is compressed to rise in internal pressure, troubles are completely eliminated, in which the polyethylene bag bursts due to rapid compression, or the polyethylene bag enters between the inner wall of the cylindrical-shaped housing and the piston. Further, there is produced an effect that since in the discharging process at the termination of the heating and compressing process, after the gate is opened, the lower surface of the piston heating means is lowered to a point distant several millimeters from the upper surface of the gate heating means to enable forcedly scraping off the cake adhering to the piston heating means, a trouble, in which the cake cannot be discharged, is completely eliminated and the cake discharging action can be sharply improved in reliability.

The invention according to claims 2 and 14 produces an effect that since waste gases generated at the time of melt sterilization and volume reduction of medical wastes with heating compression are completely deodorized-filtered by forced ventilation of an interior of the cylindrical-shaped housing and the upper portion of the gate, a room, in which the medical wastes disposal apparatus is installed, is more greatly improved in clean level than sickrooms in a hospital and can present a safe and comfortable working environment.

The invention according to claims 3 and 15 produces an effect that not only since a polyethylene bag, a polypale, cans, etc., in which medical wastes are received, can be automatically fed, labor saving is enabled in medical wastes disposal working, but also since medical wastes loaded on the bucket conveyor can be rapidly recovered when abnormality is caused in the medical wastes disposal apparatus for medical wastes, troubleshooting is greatly improved in workability, and not only since medical wastes can be shortened in cycle time by the preheating means, but also since waste gases from the medical wastes preheating device can be completely deodorized filtered by forced ventilation, the medical wastes disposal apparatus is made essentially safe and a room, in which the medical wastes disposal apparatus is installed, is more greatly improved in clean level than sickrooms in a hospital and can present a safe and comfortable working environment.

The invention according to claims 4 and 16 produces an effect that since vinyl chloride series medical wastes contained in sterilized medical wastes to make a burden can be completely classified, the sterilized medical wastes, from which vinyl chloride series wastes are removed, can be instantly put to energy recycling with grinding working or the like.

The invention according to claims 17 to 19 produces an effect that even when an oxygen scavenger contained in confectionery products or the like, which inquirers for sick people bring, is mixed into medical wastes and the oxygen scavenger originates a fire in the preheating process to cause a fire, a thermometer provided on the piercing nozzle for exhausting instantly detects abnormal temperature rise of exhaust gases to enable extinguishing a fire by blowing of nitrogen gases into a polyethylene bag and a polypale, in which medical wastes having caused a fire are received, so that the medical wastes disposal apparatus can be advanced to be made essentially safe.

The invention according to claims 6 and 20 produces an effect that while an operator has visually confirmed the presence of medical wastes on a bucket conveyor to manually stop a medical wastes disposal apparatus, electric interlocking of photoelectric switches and a sequencer enables automatically stopping a medical wastes disposal apparatus, so that it is possible to greatly attain labor saving.

The invention according to claims 21 to 23 produces an effect that since when wastes, which are smaller in outside dimension, like a can, than the cylindrical-shaped housing and received in a can, are fed to the medical wastes disposal apparatus, a fork protruding into an interior of the cylindrical-shaped housing is caused to retreat after cans or the like are loaded on the fork and the hatch is closed, it is possible to make cans or the like stable in posture and it is possible to surely compress cans or the like from thereabove, thereby enabling solving a problem that medical wastes received in cans or the like are scattered in the cylindrical-shaped housing.

The invention according to claims 8 and 24 produces an effect that since an air for preheating of medical wastes can be preheated by air friction in the friction type blower, it is possible to greatly reduce electric energy required for air heating in the hot blast generating device.

The invention according to claims 9 and 25 produces an effect that since the piercing nozzles repeat ascent and descent motions at all times while the piercing nozzles pierce a polyethylene bag or a polypale, in which medical wastes are received, to preheat the medical wastes, it is possible to evenly heat the medical wastes received in the polyethylene bag or the polypale, thereby enabling improving the preheating action greatly in reliability.

The invention according to claims 10 and 26 to 28 produces an effect that cake having been subjected to disposal of melt sterilization and volume reduction with heating compression can be surely and sequentially discharged outside by the push plate tightly joined to the gate.

The invention according to claims 11 and 29 produces an effect that since an emission source and disposal conditions of cake thus subjected to disposal can be clarified, medical wastes are subjected to disposal of heating compression by the apparatus of the invention whereby it is possible to completely solve a problem of illegal disposal of medical wastes, thus enabling greatly contributing to environmental maintenance.

The invention according to claims 12 and 30 produces an effect that the medical wastes disposal apparatus of the invention enables not only integrated control but also management of service lives and periods of maintenance of machine parts, which form the medical wastes disposal apparatus.

DESCRIPTION OF THE EMBODIMENTS

Figure 1:
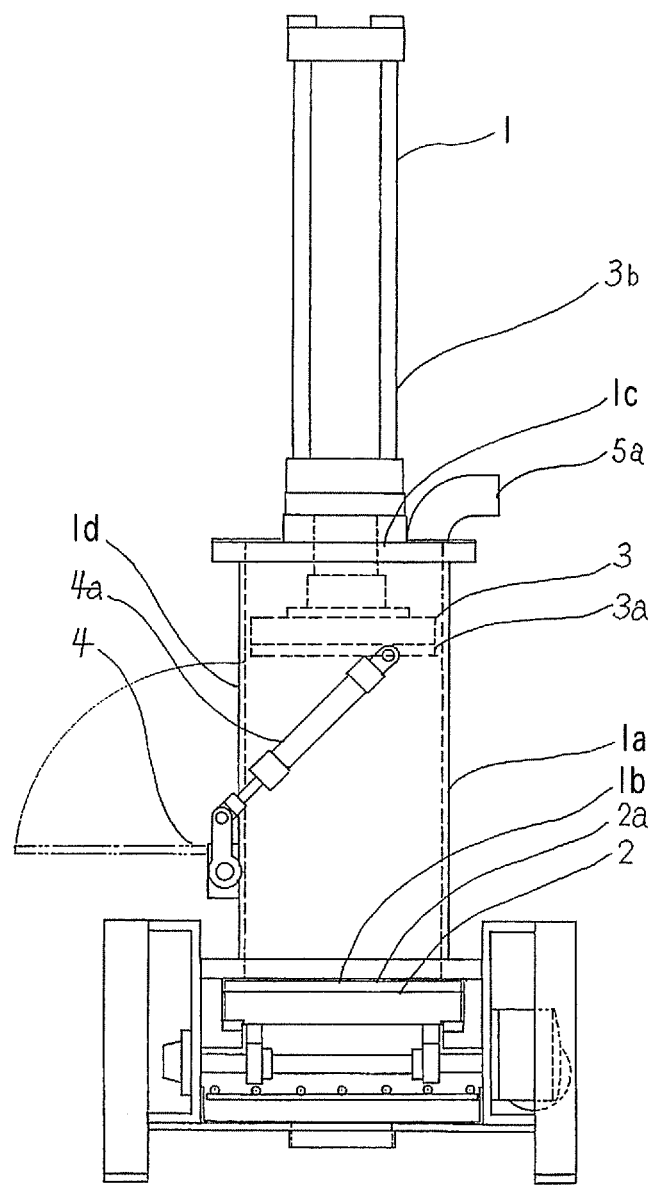
FIG. 1 is a front view showing a medical wastes disposal apparatus according to the invention.

An embodiment of the invention will be described below.

The embodiment of the invention will be described in detail with reference to the accompanying drawings. In the drawings, the same or similar constituent elements are designated by common reference characters.

Embodiment 1

Figure 2:
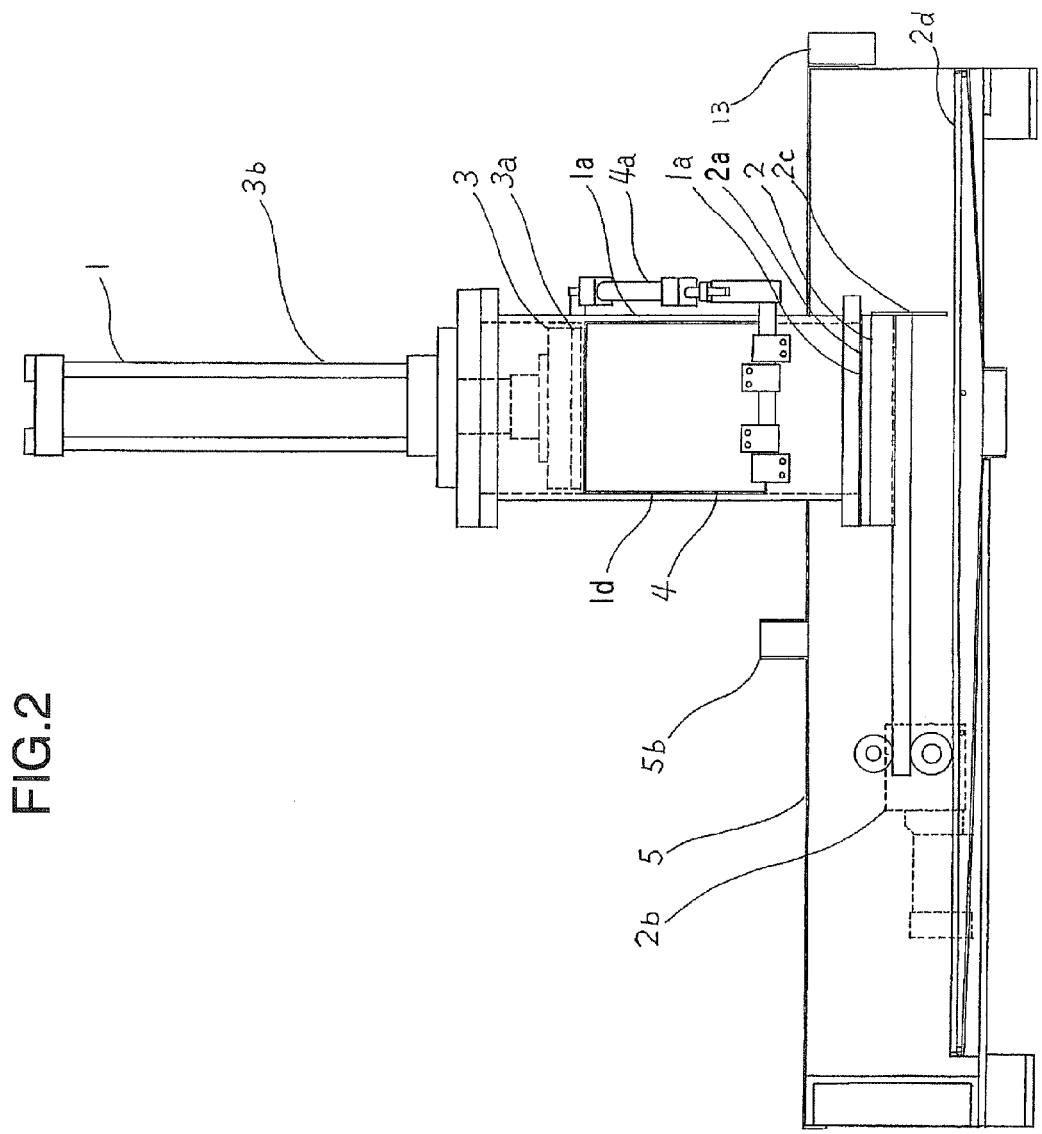
FIG. 2 is a side view showing the medical wastes disposal apparatus according to the invention.

The embodiment of the invention will be described. Referring to FIGS. 1 and 2, there is disclosed a medical wastes disposal apparatus 1 comprising a gate 2 including heating means 2a and opening and closing means 2b at a lower opening 1b on a housing lower portion of a vertical-type cylindrical-shaped housing 1a opened at both upper and lower ends thereof, a piston 3 including piston heating means 3a, which comprises heating means, and piston ascent and descent means 3b, which comprises compression means based on ascent and descent, at an upper opening 1c on an upper portion of the housing 1a, and a hatch 4 including hatch opening and closing means 4a, which comprises opening and closing means for opening and closing of a side opening 1d provided on a side of the housing 1a. When a polyethylene bag with medical wastes received therein is supplied to the cylindrical-shaped housing 1a and the piston ascent and descent means 3b, which comprises compression means, lowers the piston 3 to compress the medical wastes, the piston 3 is repeatedly caused to go up and down for stepwise compression whereby the polyethylene bag with medical wastes received therein is prevented from entering into a clearance between an inner wall of the cylindrical-shaped housing 1a and the piston 3 and from bursting due to rapid compression. When cake obtained by melt sterilization and volume reduction with heating compression is discharged, the gate 2 is fully opened to lower a lower surface of the piston heating means 3a, which comprises heating means of the piston 3, to a point distant several millimeters from an upper surface of the heating means 2a of the gate 2 and the gate 2 is closed to enable forcedly scraping off the cake adhering to the piston heating means 3a, which comprises heating means tightly joined to the piston 3.

From the viewpoint of a medical wastes disposal method, there are provided the step of supplying a polyethylene bag with medical wastes received therein to the vertical-type cylindrical-shaped housing 1a opened at both upper and lower ends thereof, the step of repeatedly causing the piston 3 to go up and down for stepwise compression to thereby prevent the polyethylene bag with medical wastes received therein from entering into the clearance between the inner wall of the cylindrical-shaped housing 1a and the piston 3 and from bursting due to rapid compression, when the piston ascent and descent means 3b being compression means of the piston 3 including the piston heating means 3a, which comprises heating means, and the piston ascent and descent means 3b, which comprises compression means based on ascent and descent, at the upper opening 1c on the upper portion of the housing 1a lowers the piston 3 to compress the medical wastes, the step of fully opening the gate 2, which includes the heating means 2a and the opening and closing means 2b at the lower opening 1b of the housing lower portion of the housing 1a, when cake obtained by melt sterilization and volume reduction with heating compression is discharged, and the step of lowering the lower surface of the piston heating means 3a, which comprises heating means of the piston 3, to a point distant several millimeters from the upper surface of the heating means 2a of the gate 2 and closing the gate 2 to enable forcedly scraping off the cake adhering to the piston heating means 3a, which comprises heating means tightly joined to the piston 3.

In addition, the specific construction of the medical wastes disposal apparatus 1 is described in detail in JP-A-7-88140 and so a further explanation is not given.

Thereby, the piston 3 is repeatedly caused to go up and down to thereby enable stepwise heating and compressing the polyethylene bag with medical wastes received therein, the polyethylene bag with medical wastes received therein is heated and compressed while gradually softening together with the medical wastes, and compression can be accomplished while appropriately exhausting an air in the bag upon ascent of the piston even when the polyethylene bag is compressed to rise in internal pressure, so that troubles are completely eliminated, in which the polyethylene bag bursts due to rapid compression, or the polyethylene bag enters into between the inner wall of the cylindrical-shaped housing 1a and the piston 3. Further, also in the discharging process at the termination of the heating and compressing process, after the gate 2 is opened, the lower surface of the piston heating means 3a, which comprises heating means for the piston 3, is lowered to a point distant several millimeters from the upper surface of the heating means 2a of the gate 2 to enable forcedly scraping off the cake adhering to the piston heating means 3a, which comprises heating means for the piston 3, so that a trouble, in which the cake cannot be discharged, is completely eliminated and the cake discharging action can be greatly improved in reliability.

Embodiment 2

Figure 6:
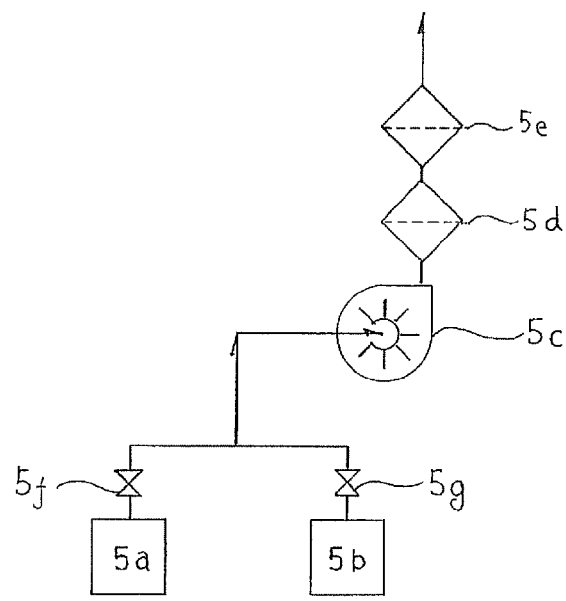
FIG. 6 is a system diagram showing a deodorization-filteration device for the medical wastes disposal apparatus according to the invention.
Figure 7:
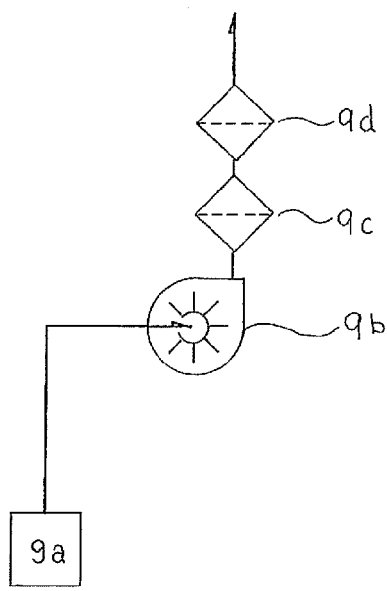
FIG. 7 is a system diagram showing the deodorization-filteration device for the medical wastes disposal apparatus according to the invention.

Subsequently, an explanation will be given to a further embodiment of the invention. Referring to FIGS. 1, 2, and 6, a nozzle 5a capable of air ventilation in a housing 1a is further provided at an upper opening 1c on an upper portion of a vertical-type cylindrical-shaped housing 1a. Further, a nozzle 5b capable of air ventilation above a gate 2 is provided on an upper portion of a gate cover 5 disposed outside gate driving means 2b, which comprises gate opening and closing means for opening and closing of a lower opening 1b on a lower portion of the housing. A blower 5c connected by way of piping to the nozzles 5a, 5b sucks gases generated in the course of heating and compressing the medical wastes and deodorizing means 5d for deodorization of gases and filtering means 5e for filtration of pathogenic bacteria are further provided at a discharge port of the blower 5c.

From the viewpoint of a medical wastes disposal method, there are provided the step of sucking gases, which are generated in the course of heating and compressing medical wastes, by means of the blower 5c connected by way of piping to the nozzles 5a, which is provided at the upper opening 1c on the upper portion of the vertical-type cylindrical-shaped housing 1a to be capable of air ventilation in the housing 1a, and the nozzles 5b being capable of air ventilation above the gate 2 and provided on the upper portion of the gate cover 5 disposed outside the gate driving means 2b, which comprises gate opening and closing means for opening and closing of the lower opening 1b on the lower portion of the housing, the step of deodorizing gases by means of the deodorizing means 5d at the discharge port of the blower 5c, and the step of filtering pathogenic bacteria by means of the filtering means 5e at the discharge port of the blower 5c.

Thereby, since waste gases generated at the time of melt sterilization and volume reduction of medical wastes with heating compression can be completely deodorized-filtered by forced ventilation of an interior of the cylindrical-shaped housing 1a and the upper portion of the gate 2, a room, in which the medical wastes disposal apparatus 1 is installed, is more greatly improved in clean level than sickrooms in a hospital and can present a safe and comfortable working environment.

Embodiment 3

Figure 3:
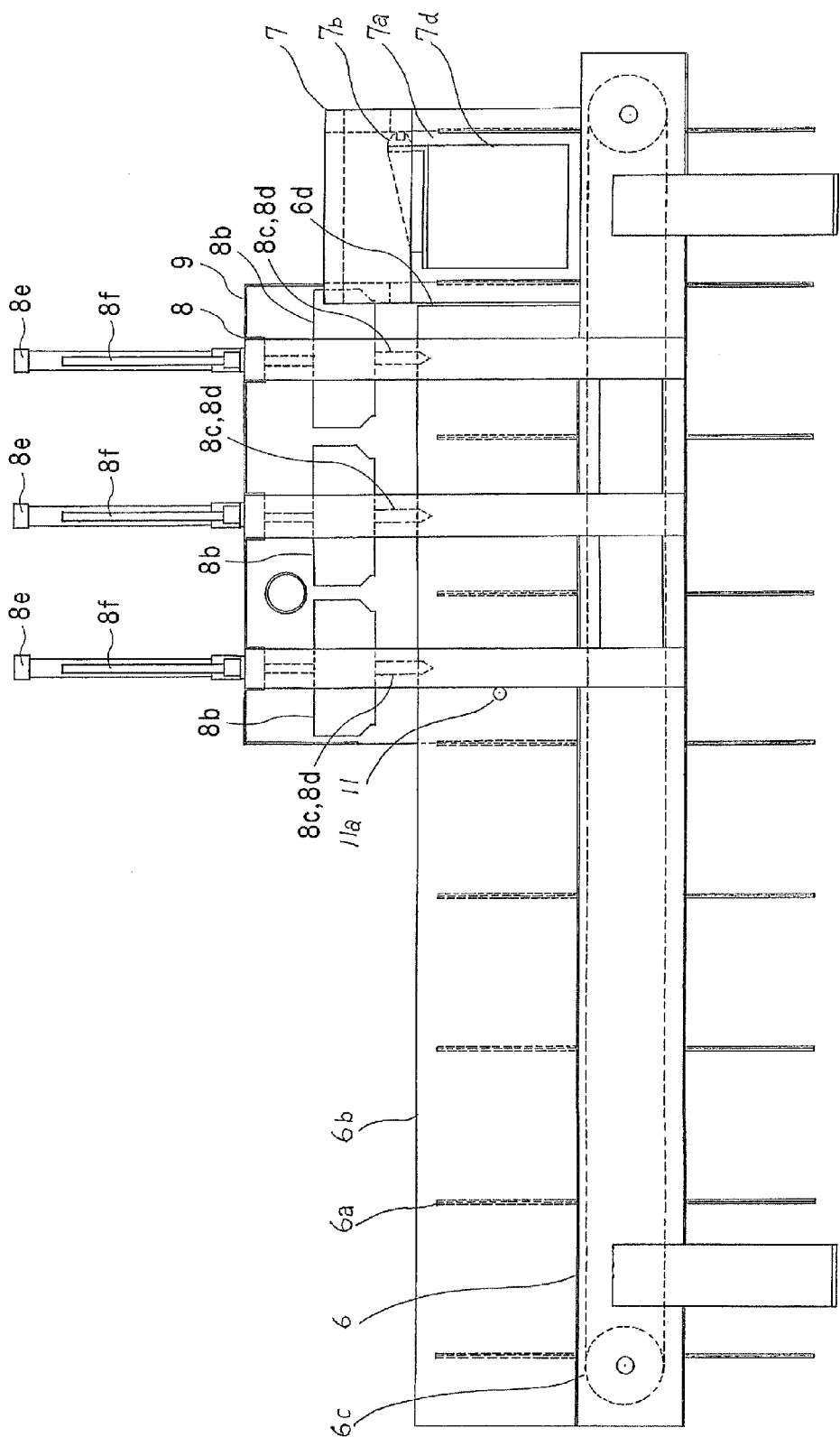
FIG. 3 is a side view showing a bucket conveyor and a medical wastes preheating device in the invention.
Figure 4:
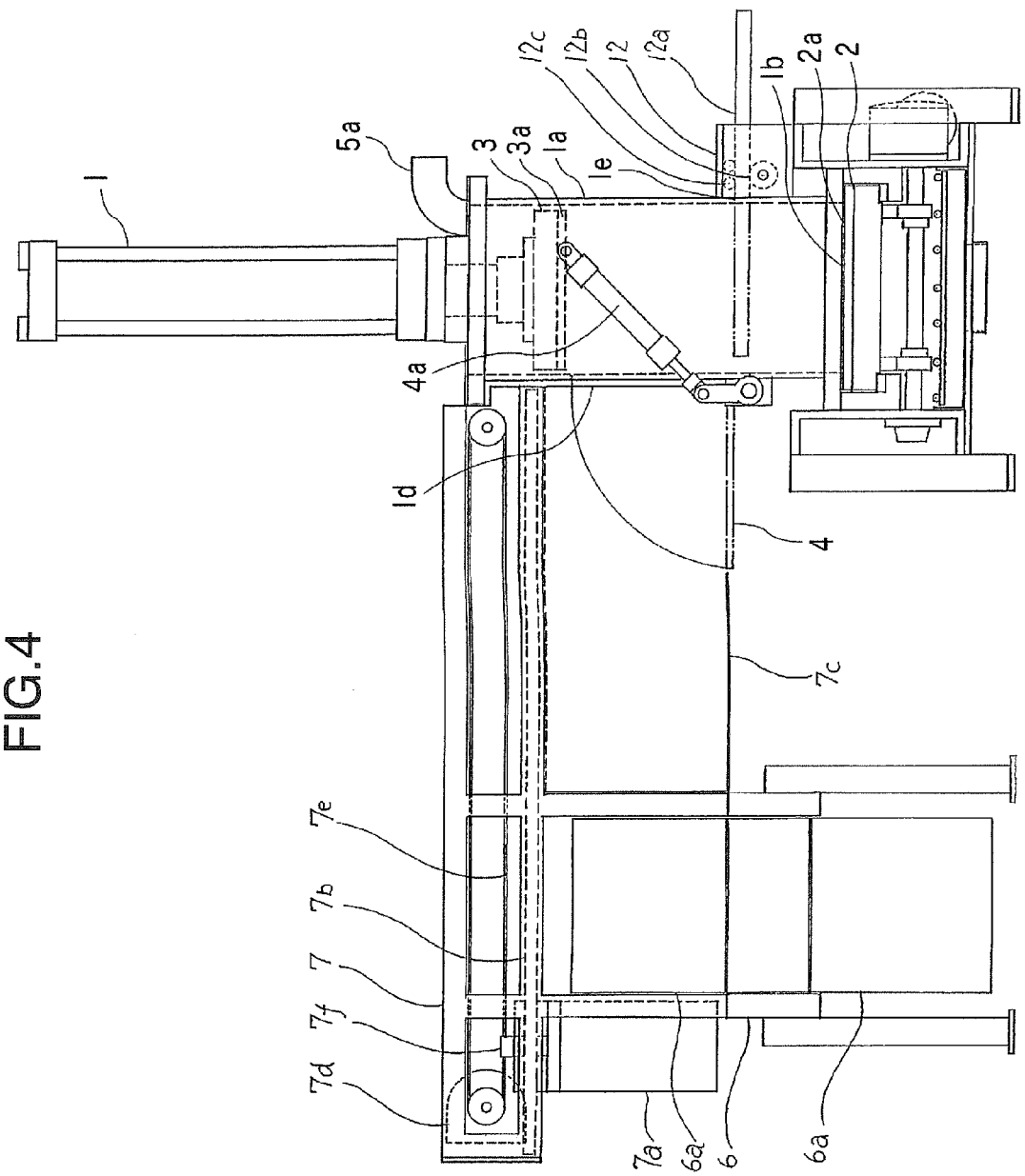
FIG. 4 is a front view showing a state when an automatic feeding device, which feeds medical wastes to the medical wastes disposal apparatus from the bucket conveyor in the invention, and the medical wastes disposal apparatus are connected to each other.

Further, a further embodiment of the invention will be described. Referring to FIGS. 3 and 4, an automatic feeding device 7 comprising a pusher mechanism being perpendicular to a bucket conveyor 6 to serve for transfer to a housing side opening 1d of a medical wastes disposal apparatus 1 from a side guide plate opening 6d at a terminal end in a traveling direction of a bucket conveyor 6, and to include a push plate 7a, a slide guide 7b, a chute 7c, a drive motor 7d, a timing belt 7e, and a connection fitting 7f is further provided on the bucket conveyor 6 comprising conveyor driving means 6c, which comprises traveling means capable of traveling in a traveling direction of the conveyor 6, and buckets formed by bottomed partition plates 6a having regular intervals and a particular height and side guide plates 6b of a particular height arranged on conveyor frames on both sides in a traveling direction of the conveyor 6. Whenever a polyethylene bag, a polypale, cans, etc., in which medical wastes are received, are loaded in a bucket of the bucket conveyor 6 and a disposal cycle of medical wastes is completed in the medical wastes disposal apparatus 1, the bucket conveyor 6 advances one bucket by one bucket and stops, medical wastes loaded in the bucket are automatically fed to the medical wastes disposal apparatus 1 by means of the pusher mechanism, and when abnormality is caused in the bucket conveyor 6, the bucket conveyor 6 is caused to continuously advance or retreat, thereby enabling taking out medical wastes loaded in the bucket of the bucket conveyor 6.

From the viewpoint of a medical wastes disposal method, there are provided the step of loading a polyethylene bag, a polypale, cans, etc., in which medical wastes are received, in the bucket of the bucket conveyor 6 comprising the conveyor driving means 6c, which comprises traveling means capable of traveling in the traveling direction of the bucket conveyor 6, and buckets, which are formed by bottomed partition plates 6a having regular intervals and a particular height and side guide plates 6b of a particular height arranged on conveyor frames on both sides in a traveling direction of the bucket conveyor 6, the step of causing the bucket conveyor 6 to advance one bucket by one bucket and stop whenever a disposal cycle of medical wastes is completed in the medical wastes disposal apparatus 1, the step of automatically feeding medical wastes loaded in the bucket to the medical wastes disposal apparatus 1 by means of the pusher mechanism of the automatic feeding device 7 comprising the pusher mechanism for transfer of medical wastes loaded in the bucket to the housing side opening 1d of the medical wastes disposal apparatus 1 from the side guide plate opening 6d at a terminal end in the traveling direction of the bucket conveyor 6 and including the push plate 7a, the slide guide 7b, the chute 7c, the drive motor 7d, the timing belt 7e, and the connection fitting 7f, and the step of causing the bucket conveyor 6 to continuously advance or retreat when abnormality is caused in the bucket conveyor 6, thereby enabling taking out medical wastes loaded in the bucket of the bucket conveyor 6.

In addition, the specific construction of the bucket conveyor 6 is described in detail in JP-U-6-42819 and so a further explanation is not given.

Thereby, not only since a polyethylene bag, a polypale, cans, etc., in which medical wastes are received, can be automatically fed, labor saving is enabled in medical wastes disposal working, but also since medical wastes loaded on the bucket conveyor 6 can be rapidly recovered when abnormality is caused in the medical wastes disposal apparatus 1 for medical wastes, troubleshooting is greatly improved in workability.

Embodiment 4

Figure 5:
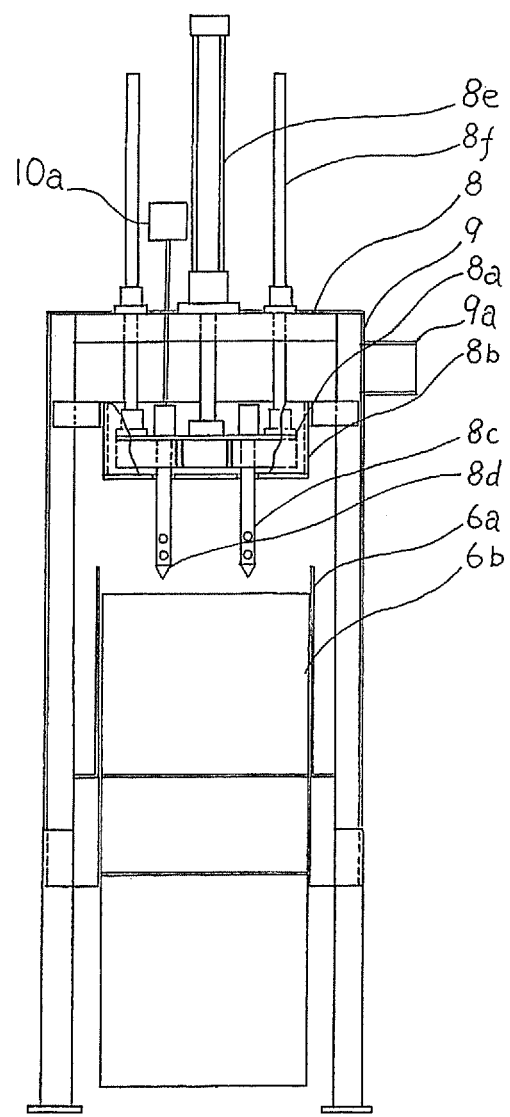
FIG. 5 is a front view showing the medical wastes preheating device according to the invention.
Figure 8:
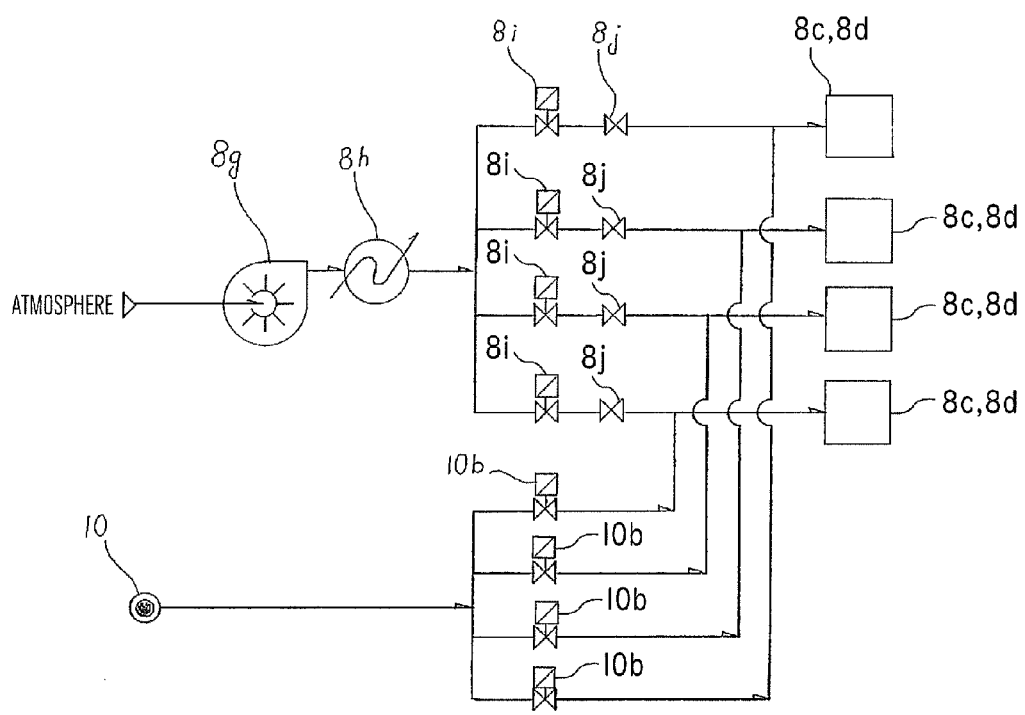
FIG. 8 is a view showing a piping system of the medical wastes preheating device according to the invention.

Also, a further embodiment of the invention will be described. Referring to FIGS. 5 and 8, there is further provided a medical wastes preheating device 8 formed by tightly joining piercing nozzles 8c, 8d for hot air blasting and for exhausting to a lower portion of a moving plate 8a provided with driving means 8e, which comprises ascent and descent means capable of going up and down in a vertical direction, and connecting, by way of piping, between the piercing nozzles 8c, 8d and a hot blast generating device provided with an air heater 8h, which comprises hot blast temperature adjusting means capable of adjusting a hot blast temperature. The piercing nozzles 8c, 8d pierce a polyethylene bag and a polypale, in which medical wastes are received and which are loaded in a bucket of a bucket conveyor 6, the medical wastes are preheated by hot air blasting of the hot blast generating device to be shortened in cycle time, a cover 9 with an exhaust nozzle 9a covers the periphery of a moving plate 8a provided with ascent and descent means, which is capable of going up and down in a vertical direction, and the exhaust nozzle 9a of the cover 9 is connected by way of piping to a suction port of a blower 9b provided at an exhaust port thereof with a deodorizing filter 9c, which comprises deodorizing means for deodorization of gases, and a bacteria eliminating filter 9d, which comprises filtering means for filtration of pathogenic bacteria, so that it is possible to deodorize and filter exhaust gases generated from the piercing nozzles 8c, 8d, for exhaust, tightly joined to the moving plate 8a.

From the viewpoint of a medical wastes disposal method, there are provided the step of piercing a polyethylene bag and a polypale, in which medical wastes are received and which are loaded in the bucket of the bucket conveyor 6, with the piercing nozzles 8c, 8d of the medical wastes preheating device 8 formed by tightly joining the piercing nozzles 8c, 8d for hot air blasting and for exhausting to a lower portion of the moving plate 8a provided with driving means 8e, which comprises ascent and descent means capable of going up and down in a vertical direction, and connecting, by way of piping, between the piercing nozzles 8c, 8d and the hot blast generating device provided with the air heater 8h, which comprises hot blast temperature adjusting means capable of adjusting a hot blast temperature, to preheat medical wastes by hot air blasting of the hot blast generating device to achieve shortening in cycle time, and the step of enabling deodorizing and filtering exhaust gases generated from the piercing nozzles 8*c*, 8*d*, for exhaust, tightly joined to the moving plate 8*a* by using the cover 9 with the exhaust nozzle 9*a* to cover the periphery of the moving plate 8*a* provided with driving means 8*e*, which comprises ascent and descent means capable of going up and down in the vertical direction, and connecting, by way of piping, between the exhaust nozzle 9*a* of the cover 9 and the suction port of the blower 9*b* provided at an exhaust port thereof with the deodorizing filter 9*c*, which comprises deodorizing means for deodorization of gases, and the bacteria eliminating filter 9*d*, which comprises filtering means for filtration of pathogenic bacteria.

In addition, the specific construction of the medical wastes preheating device 8 is described in detail in JP-A-2001-252345 and so a further explanation is not given.

Thereby, not only since medical wastes can be shortened in cycle time by the preheating means, but also since waste gases from the medical wastes preheating device can be completely deodorized-filtered by forced ventilation, the medical wastes disposal apparatus 1 can be made essentially safe and a room, in which the medical wastes disposal apparatus 1 is installed, is more greatly improved in clean level than sickrooms in a hospital and can present a safe and comfortable working environment.

Embodiment 5

Further, a further embodiment of the invention will be described. Referring to FIG. 3, it is possible with a medical wastes preheating device 8 to subject medical wastes to sterilization by heat only with hot blast, to discharge medical wastes from a bucket conveyor 6 not via a medical wastes disposal apparatus 1, and to manually classify contents of medical wastes into vinyl chloride series and non-vinyl chloride series.

From the viewpoint of a medical wastes disposal method, there are further provided the step of using the medical wastes preheating device 8 to subject medical wastes to sterilization by heat only with hot blast, and the step of discharging medical wastes from the bucket conveyor 6 not via the medical wastes disposal apparatus 1, so that it is made possible to manually classify contents of medical wastes into vinyl chloride series and non-vinyl chloride series.

Thereby, since vinyl chloride series medical wastes contained in sterilized medical wastes to make a burden can be completely classified, the sterilized medical wastes, from which vinyl chloride series wastes are removed, can instantly be subjected to energy recycling with grinding working or the like.

Embodiment 6

Also, a further embodiment of the invention will be described. Referring to FIGS. 5 and 8, nitrogen gas supply pipes provided with electrically shut-off electromagnetic valves 10*b* are further connected by way of piping to piercing nozzles 8*c*, 8*d* for hot air blasting, which are tightly joined to moving plates 8*a* provided with driving means 8*e*, which comprises ascent and descent means capable of going up and down in a vertical direction. Also, temperature detectors 10*a* comprising a thermometer for detection of abnormal temperature rise of exhaust gases are further provided on the piercing nozzles 8*d* for exhausting, and in the case where hot blast is blown into a polyethylene bag and a polypale to thereby originate a fire in an oxygen scavenger mixed into medical wastes to cause a fire, the temperature detectors 10*a* comprising a thermometer detect abnormal temperature rise of exhaust gases and the electromagnetic valves 10*b* on the nitrogen gas supply pipes are electrically interlockingly opened to permit nitrogen gases in a nitrogen bomb 10 to be blown into the polyethylene bag and the polypale whereby it is possible to automatically extinguish a fire caused in the polyethylene bag and the polypale.

From the viewpoint of a medical wastes disposal method, there are provided the step of detecting abnormal temperature rise of exhaust gases with the use of the temperature detectors 10*a* comprising a thermometer, for detection of abnormal temperature rise of exhaust gases, provided on the piercing nozzles 8*d* for exhausting, in the case where hot blast is blown into a polyethylene bag and a polypale to thereby originate a fire in an oxygen scavenger mixed into medical wastes to cause a fire, and the step, in which the electromagnetic valves 10*b* on the nitrogen gas supply pipes provided with the electrically shut-off electromagnetic valves 10*b* open electrically interlocking with the piercing nozzles 8*c*, 8*d* tightly jointed to the moving plates 8*a* provided with the driving means 8*e*, which comprises ascent and descent means capable of going up and down in the vertical direction, to permit nitrogen gases in the nitrogen bomb 10 to be blown into the polyethylene bag and the polypale whereby it is possible to automatically extinguish a fire caused in the polyethylene bag and the polypale.

Thereby, even when an oxygen scavenger contained in confectionery products or the like, which inquirers for sick people bring, is mixed into medical wastes and the oxygen scavenger originates a fire in the preheating process to cause a fire, the temperature detectors 10*a* comprising the thermometers 1 provided on the piercing nozzles 8*d* for exhausting instantly detect abnormal temperature rise of exhaust gases to enable extinguishing a fire by blowing of nitrogen gases into a polyethylene bag and a polypale, in which medical wastes having caused a fire are received, so that the medical wastes disposal apparatus 1 can be made essentially safe.

Embodiment 7

Further, a further embodiment of the invention will be described. Referring to FIG. 3, holes 11 for photoelectric switches are further provided on the same axis on both sides of side guide plates 6*b* of a bucket conveyor 6. Further, a pair of photoelectric switches 11*a* are arranged in positions, in which light can transmit through the holes 11, for photoelectric switches, in the holes 11, for photoelectric switches, of the side guide plates 6*b*, the photoelectric switches 11 detect the presence of a polyethylene bag, a polypale, cans, etc., in which medical wastes are received, in a bucket of a bucket conveyor 6 to enable automatically and sequentially stopping a medical wastes preheating device 8, the bucket conveyor 6, and a medical wastes disposal apparatus 1 at the completion of disposals of a predetermined number of cycles.

From the viewpoint of a medical wastes disposal method, there are provided the step of detecting the presence of a polyethylene bag, a polypale, cans, etc., in which medical wastes are received, in a bucket of the bucket conveyor 6 with the use of a pair of photoelectric switches 11 arranged in positions, in which light can transmit through the holes 11 for photoelectric switches, on the same axis on both sides of the side guide plates 6*b* of the bucket conveyor 6, and the step of enabling automatically and sequentially stopping the medical wastes preheating device 8, the bucket conveyor 6, and the medical wastes disposal apparatus 1 at the completion of disposals of a predetermined number of cycles.

Thereby, while an operator has visually confirmed the presence of medical wastes on the bucket conveyor 6 to manually stop the medical wastes disposal apparatus 1, electric interlocking of the photoelectric switches 11*a* and a sequencer enables automatically stopping the medical wastes disposal apparatus 1, so that it is possible to greatly attain labor saving.

Embodiment 8

Also, a further embodiment of the invention will be described. Referring to FIG. 4, a side hole 1e is further provided on a lower portion of a vertical-type cylindrical-shaped housing, a fork mechanism 12 provided with driving means 12b, which comprises drawing and entering means capable of drawing out of and entering into the side hole 1e, is further provided, when a polypale or cans, etc., in which medical wastes are received, are fed from a side opening 1d on a side of a vertical-type cylindrical-shaped housing 1a, a toothed rack 12a, which comprises a fork of the fork mechanism 12, is caused by the use of driving means 12b and a guide roller 12c to advance into an interior of a housing 1a to receive a polypale or cans on the toothed rack 12a, and after a hatch 4 for the side opening 1d is closed, the toothed rack 12a, which comprises a fork, is caused to retreat to enable loading a polypale or cans on that gate heating means 2a of a gate 2, which is disposed at a lower opening 1b of a housing lower portion, without tipping.

From the viewpoint of a medical wastes disposal method, there are provided the step of using, at the time of feeding a polypale, cans, etc., in which medical wastes are received, from the side opening 1d on a side of the vertical-type cylindrical-shaped housing 1a, the driving means 12b and the guide roller 12c to advance the toothed rack 12a, which comprises a fork of the fork mechanism 12 provided with the driving means 12b, which comprises drawing-out and entering means capable of drawing out of and entering into the side hole 1e provided on the lower portion of the vertical-type cylindrical-shaped housing, into an interior of the housing 1a to receive a polypale or cans on the fork, and the step of, after the hatch 4 for the side opening 1d is closed, retreating the toothed rack 12a, which comprises a fork, to enable loading a polypale or cans on that gate heating means 2a of the gate 2, which is disposed at the lower opening 1b of the housing lower portion, without tipping.

In addition, the specific construction of the fork mechanism 12 is described in detail in JP-U-3126377 and so a further explanation is not given.

Thereby, when wastes, which are smaller in outside dimension, like a can, than the cylindrical-shaped housing 1a and received in cans or the like, are fed to the medical wastes disposal apparatus 1, the toothed rack 12a, which comprises a fork protruding into the cylindrical-shaped housing 1a, is caused to retreat after cans or the like are loaded on the toothed rack 12a after the hatch is closed, so that it is possible to make cans or the like stable in posture and it is possible to surely compress cans or the like from thereabove, thereby enabling solving a problem that medical wastes received in cans or the like are scattered in the cylindrical-shaped housing 1a.

Embodiment 9

Further, a further embodiment of the invention will be described. Referring to FIG. 8, a friction type blower 8g is further provided on a hot blast generating device of a medical wastes preheating device 8. Thereby, an air is preheated by frictional heat generated in the friction type blower 8g, so that it is possible to reduce electric energy for air heating in the hot blast generating device.

From the viewpoint of a medical wastes disposal method, there is provided the step of preheating an air by means of frictional heat in the friction type blower 8g provided on the hot blast generating device of the medical wastes preheating device 8, thereby enabling reducing electric energy for air heating in the hot blast generating device.

Thereby, since an air for preheating of medical wastes can be preheated by air friction in the friction type blower 8g, it is possible to greatly reduce electric energy required for air heating in the hot blast generating device. Actually, when a vortex blower VB-060 manufactured by Hitachi Machinery-Producing System Company was used as the friction type blower 8g, a temperature difference between an inlet air and an outlet air was about 60° C. This amounts to one-third as high as an air heating temperature 180° C.

Embodiment 10

Also, a further embodiment of the invention will be described. Referring to FIG. 5, in a process, in which piercing nozzles 8c, 8d for hot air blasting and for exhausting, tightly joined to a moving plate provided with driving means 8e, which comprises ascent and descent means capable of going up and down in a vertical direction of a medical wastes preheating device 8, are caused to pierce a polyethylene bag or a polypale to bring about preheating, the moving plate goes up and down at all times to enable evenly heating medical wastes in the polyethylene bag or the polypale.

From the viewpoint of a medical wastes disposal method, there is provided the step of causing the moving plate to go up and down at all times to enable evenly heating medical wastes in a polyethylene bag or a polypale in a process, in which the piercing nozzles 8c, 8d for hot air blasting and for exhausting, tightly joined to the moving plate provided with the driving means 8e, which comprises ascent and descent means capable of going up and down in the vertical direction of the medical wastes preheating device 8, are caused to pierce a polyethylene bag or a polypale to bring about preheating.

Thereby, since the piercing nozzles 8c, 8d repeat ascent and descent motions at all times while the piercing nozzles 8c, 8d pierce a polyethylene bag or a polypale, in which medical wastes are received, to preheat the medical wastes, it is possible to evenly heat the medical wastes received in the polyethylene bag or the polypale, thereby enabling improving the preheating action greatly in reliability.

Embodiment 11

Further, a further embodiment of the invention will be described. Referring to FIGS. 1 and 2, a drain-board 2d is further arranged below a gate 2 at a lower opening 1b on a lower portion of a vertical-type cylindrical-shaped housing to receive cake obtained by melt sterilization and volume reduction of medical wastes with heating compression. A push plate 2c is further tightly joined to the gate 2 to enable maintaining a predetermined spacing between it and the drain-board 2d. Cake dropping upon opening of the gate 2 can be automatically discharged outside by the push plate 2c tightly joined to the gate 2 when the gate 2 is closed.

From the viewpoint of a medical wastes disposal method, there is provided the step of enabling automatically discharging outside cake dropping upon opening of the gate, when the gate 2 is closed, by the use of the push plate 2c tightly joined to the gate 2, which push plate 2c is capable of maintaining a predetermined spacing between it and the drain-board 2d arranged below the gate 2 at the lower opening 1b of the lower portion of the vertical-type cylindrical-shaped housing to receive cake obtained by melt sterilization and volume reduction of medical wastes with heating compression.

Thereby, cake having been subjected to disposal of melt sterilization and volume reduction with heating compression can be surely and sequentially discharged outside by the push plate 2c tightly joined to the gate 2.

Embodiment 12

Also, a further embodiment of the invention will be described. Referring to FIG. 1, a bar code or a quick response code is further stuck to medical wastes, which are received in a polyethylene bag, a polypale, cans, etc., every department of diagnosis and treatment, from which the medical wastes are discharged. When the medical wastes are loaded in a bucket of a bucket conveyor 6, the bar code or quick response code is read, and after the medical wastes are subjected to disposal of melt sterilization and volume reduction with heating compression, information of emission source, disposal conditions of a medical wastes preheating device 8 and a medical wastes disposal apparatus 1, etc. are automatically written on an electronic tag and the electronic tag is automatically stuck to cake, which is obtained by disposal, by means of an IC tag sticking device to enable certifying that the medical wastes have been properly subjected to disposal.

From the viewpoint of a medical wastes disposal method, there are provided the step of reading bar codes or quick response codes stuck to medical wastes, which are received in a polyethylene bag, a polypale, cans, etc., every department of diagnosis and treatment, from which medical wastes are discharged, when the medical wastes are loaded in buckets of the bucket conveyor 6, and the step of automatically writing information of emission source, disposal conditions of the medical wastes preheating device and the medical wastes disposal apparatus 1, etc. on electronic tags, after the medical wastes are subjected to disposal of melt sterilization and volume reduction with heating compression, to automatically stick the electronic tags to cake, which is obtained by disposal, by means of the IC tag sticking device to enable certifying that medical wastes have been properly subjected to disposal. Since bar codes, quick response codes, and an IC tag sticking device are conventionally used, they are not described further.

Thereby, since an emission source and disposal conditions of cake being thus subjected to disposal can be clarified, medical wastes are subjected to disposal of heating compression by the apparatus of the invention whereby it is possible to completely solve a problem of illegal disposal of medical wastes, thus enabling greatly contributing to environmental maintenance.

Embodiment 13

Also, a further embodiment of the invention will be described. Referring to FIGS. 3 and 4, a bucket conveyor 6, a medical wastes preheating device 8, and a medical wastes disposal apparatus 1 are electrically interlocked to enable exercising integrated control by means of a programmable sequencer and a touch panel display electrically interlocked with the programmable sequencer.

From the viewpoint of a medical wastes disposal method, there is provided the step of electrically interlocking the bucket conveyor 6, the medical wastes preheating device 8, and the medical wastes disposal apparatus 1 together to enable exercising integrated control by means of the programmable sequencer and the touch panel display electrically interlocked with the programmable sequencer. Since a programmable sequencer and a touch panel display are conventionally used, they are not described further.

Thereby, the medical wastes disposal apparatus 1 of the invention enables not only integrated control but also management of service lives and periods of maintenance of machine parts, which form the medical wastes disposal apparatus 1.

INDUSTRIAL APPLICABILITY

According to the invention, it is possible to present to medical institutions and traders interested for disposal of medical wastes a high medical wastes disposal method and a high medical wastes disposal apparatus capable of meeting various problems existing in the prior medical wastes disposal methods, such as work safety ensuring, pollution control of atmosphere and water quality, nature environmental maintenance, energy recycling, etc., to say nothing of sure disposal of melt sterilization and volume reduction.

Further, according to the invention, infectious medical wastes, which have been liable to be subjected to illegal disposal, can be surely subjected to melt sterilization and volume reduction and made harmless in a hospital being an emission source, and social responsibility can be fulfilled not to cause a problem of environment pollution or the like.

The invention claimed is:
1. A medical wastes disposal apparatus comprising:
a gate including heating means and opening and closing means on a housing lower portion of a vertical-type cylindrical-shaped housing opened at both upper and lower ends thereof,
a piston including heating means and compression means based on ascent and descent on an upper portion of the housing,
a hatch including opening and closing means for opening and closing of a side opening provided on a side of the housing,
a drain-board arranged below the gate on the lower portion of the vertical-type cylindrical-shaped housing to receive cake obtained by melt sterilization and volume reduction of medical wastes with heating compression and a push plate tightly joined to the gate to enable maintaining a predetermined spacing between the push plate and the drain-board and wherein cake dropping upon opening of the gate can be automatically discharged outside by the push plate tightly joined to the gate when the gate is closed, and
a side hole provided on the lower portion of the vertical-type cylindrical-shaped housing and a fork mechanism provided with drawing and entering means, which is capable of drawing out of and entering into the side hole and wherein when a polypale or cans in which medical wastes are received, are fed from the side opening on the side of the vertical-type cylindrical-shaped housing, a fork of the fork mechanism is caused to advance into an interior of the housing to receive the polypale or cans on the fork, and after the hatch for the side opening is closed, the fork is caused to retreat to enable loading the polypale or cans on the gate, which is disposed on the housing lower portion, without tipping,
wherein when a polyethylene bag with medical wastes received therein is supplied to the cylindrical-shaped housing and the compression means lowers the piston to compress the medical wastes, the piston is repeatedly caused to go up and down for stepwise compression whereby the polyethylene bag with medical wastes received therein is prevented from entering into a clear- ance between an inner wall of the cylindrical-shaped housing and the piston and from bursting due to rapid compression, and when a cake obtained by melt sterilization and volume reduction with heating compression is discharged, the gate is fully opened to lower a lower surface of the heating means of the piston to a point adjacent to an upper surface of the heating means of the gate and the gate is closed to enable forcibly scraping off the cake adhering to the heating means tightly joined to the piston.

2. The medical wastes disposal apparatus according to claim 1, further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower.

3. The medical wastes disposal apparatus according to claim 1, further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and wherein whenever a polyethylene bag, a polypale, or cans in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, and a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and wherein the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate.

4. The medical wastes disposal apparatus according to claim 1, further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and wherein whenever a polyethylene bag, a polypale, or cans in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and wherein the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein it is possible to subject medical wastes to disposal of sterilization by heat only with hot blast by means of the medical wastes preheating device, to discharge the medical wastes from the bucket conveyor not via the medical wastes disposal apparatus, and to manually classify contents of the medical wastes into vinyl chloride series and non-vinyl chloride series.

5. The medical wastes disposal apparatus according to claim 1, wherein a nitrogen gas supply pipe provided with an electrically shut-off electromagnetic valve is further connected by way of piping to a piercing nozzle for hot air blasting, which nozzle is tightly joined to a moving plate provided with ascent and descent means, which is capable of going up and down in the vertical direction, a thermometer for detection of abnormal temperature rise of exhaust gases is further provided on a piercing nozzle for exhausting, and in the case where hot blast is blown into a polyethylene bag and a polypale to thereby originate a fire in an oxygen scavenger mixed into medical wastes to cause a fire, the thermometer detects abnormal temperature rise of exhaust gases and the electromagnetic valve on the nitrogen gas supply pipe is electrically interlockingly opened to permit nitrogen gases to be blown into the polyethylene bag and the polypale whereby it is possible to automatically extinguish a fire caused in the polyethylene bag and the polypale.

6. The medical wastes disposal apparatus according to claim 1, further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and wherein whenever a polyethylene bag, a polypale, or cans in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and wherein the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, and holes, for photoelectric switches, provided on the same axis on both sides of the side guide plates of the bucket conveyor, and a pair of photoelectric switches arranged in positions, in which light can transmit through the holes, in the holes of the side guide plates and wherein the photoelectric switches detect the presence of a polyethylene bag, a polypale, or cans in which medical wastes are received, in a bucket of the bucket conveyor to enable automatically and sequentially stopping the medical wastes preheating device, the bucket conveyor, and the medical wastes disposal apparatus at the completion of disposals of a predetermined number of cycles.

7. The medical wastes disposal apparatus according to claim 1, further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and wherein whenever a polyethylene bag, a polypale, or cans in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and wherein the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein a friction type blower is further provided on the hot blast generating device of the medical wastes preheating device to enable preheating an air by means of frictional heat generated in the friction type blower to reduce electric energy for air heating in the hot blast generating device.

8. The medical wastes disposal apparatus according to claim 1, further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and wherein whenever a polyethylene bag, a polypale, or cans in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and wherein the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein in a process, in which the piercing nozzles for hot air blasting and for exhausting, tightly joined to the moving plate provided with ascent and descent means, which is capable of going up and down in the vertical direction of the medical wastes preheating device, are caused to pierce a polyethylene bag or a polypale to bring about preheating, the moving plate goes up and down at all times to enable evenly heating medical wastes in the polyethylene bag or the polypale.

9. The medical wastes disposal apparatus according to claim 1, further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and wherein whenever a polyethylene bag, a polypale, or cans in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and wherein the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein a bar code or a quick response code is further stuck to medical wastes, which are received in a polyethylene bag, a polypale, cans every department of diagnosis and treatment, from which the medical wastes are discharged, when the medical wastes are loaded in the bucket of the bucket conveyor, the bar code or quick response code is read, and after the medical wastes are subjected to disposal of melt sterilization and volume reduction with heating compression, the information of emission source, disposal conditions of the medical wastes preheating device and the medical wastes disposal apparatus are automatically written on an electronic tag and the electronic tag is automatically stuck to cake, which is obtained by disposal, by means of an IC tag sticking device to enable certifying that the medical wastes have been properly subjected to disposal.

10. The medical wastes disposal apparatus according to claim 1, further comprising a nozzle provided on the housing upper portion of the vertical-type cylindrical-shaped housing to be capable of air ventilation in the housing, a nozzle provided outside and above gate opening and closing means for opening and closing of the housing lower portion to be capable of air ventilation in the upper portion of the gate, deodorizing means, which sucks gases generated by a blower connected by way of piping to the nozzles in the course of heating compression of medical wastes to deodorize gases, and filtering means for filtration of pathogenic bacteria, the deodorizing means and the filtering means being provided at a discharge port of the blower, an automatic feeding device provided on a bucket conveyor, which comprises traveling means capable of traveling in a traveling direction of the conveyor and buckets formed by bottomed partition plates having regular intervals and a particular height and side guide plates of a particular height arranged on conveyor frames on both sides in the traveling direction of the conveyor, the automatic feeding device comprising a pusher mechanism being perpendicular to the bucket conveyor to serve for transfer to the housing side opening of the medical wastes disposal apparatus from a side guide plate opening at a terminal end in the traveling direction of the bucket conveyor, and wherein whenever a polyethylene bag, a polypale, or cans in which medical wastes are received, are loaded in a bucket of the bucket conveyor and a disposal cycle of medical wastes is completed in the medical wastes disposal apparatus, the bucket conveyor advances one bucket by one bucket and stops, the medical wastes loaded in the bucket are automatically fed to the medical wastes disposal apparatus by means of the pusher mechanism, and when abnormality is caused in the bucket conveyor, the bucket conveyor is caused to continuously advance or retreat to enable taking out the medical wastes loaded in the bucket of the bucket conveyor, a medical wastes preheating device formed by tightly joining piercing nozzles for hot air blasting and for exhausting to a lower portion of a moving plate provided with ascent and descent means, which is capable of going up and down in a vertical direction, and connecting, by way of piping, between the piercing nozzles and a hot blast generating device provided with hot blast temperature adjusting means, which is capable of adjusting a hot blast temperature, and wherein the piercing nozzles pierce a polyethylene bag and a polypale, in which medical wastes are received and which are loaded in the bucket of the bucket conveyor, medical wastes are preheated by hot air blasting of the hot blast generating device to be shortened in cycle time, a cover with an exhaust nozzle covers the periphery of a moving plate provided with ascent and descent means, which is capable of going up and down in the vertical direction, the exhaust nozzle of the cover is connected by way of piping to a suction port of a blower provided at an exhaust port thereof with deodorizing means for deodorization of gases and filtering means for filtration of pathogenic bacteria, and it is possible to deodorize and filter exhaust gases generated from the piercing nozzles, for exhaust, tightly joined to the moving plate, wherein the bucket conveyor, the medical wastes preheating device, and the medical wastes disposal apparatus are electrically interlocked to enable exercising integrated control by means of a programmable sequencer and a touch panel display electrically interlocked with the programmable sequencer.

* * * * *